United States Patent
Matoba et al.

(10) Patent No.: US 7,436,926 B2
(45) Date of Patent: Oct. 14, 2008

(54) FLUORESCENT X-RAY ANALYSIS APPARATUS

(75) Inventors: Yoshiki Matoba, Chiba (JP); Takayuki Fukai, Chiba (JP); Masanori Takahashi, Chiba (JP); Yutaka Ikku, Chiba (JP)

(73) Assignee: SII Nano Technology Inc., Chiba (JP)

( * ) Notice: Subject to any disclaimer, the term of this patent is extended or adjusted under 35 U.S.C. 154(b) by 0 days.

(21) Appl. No.: 11/799,992

(22) Filed: May 3, 2007

(65) Prior Publication Data

US 2007/0269004 A1    Nov. 22, 2007

Related U.S. Application Data

(63) Continuation of application No. PCT/JP2005/019658, filed on Oct. 26, 2005.

(51) Int. Cl.
*G01N 23/223* (2006.01)
(52) U.S. Cl. .............................. 378/45; 378/44; 378/208
(58) Field of Classification Search ............. 378/44–50, 378/156–159, 208
See application file for complete search history.

(56) References Cited

U.S. PATENT DOCUMENTS

| | | | | |
|---|---|---|---|---|
| 4,720,842 A * | 1/1988 | Kira et al. | ...................... | 378/49 |
| 5,157,704 A * | 10/1992 | Harding | ...................... | 378/119 |
| 5,253,280 A * | 10/1993 | Mizuta | ...................... | 378/45 |
| 5,365,563 A * | 11/1994 | Kira et al. | ...................... | 378/48 |
| 5,712,891 A * | 1/1998 | Benony et al. | ................. | 378/47 |
| 5,832,054 A * | 11/1998 | Kuwabara | ..................... | 378/45 |
| 5,898,752 A * | 4/1999 | Van Der Wal | ................. | 378/49 |
| 5,978,442 A * | 11/1999 | Kuwabara | ..................... | 378/46 |
| 5,982,847 A * | 11/1999 | Nelson | .......................... | 378/47 |
| 6,012,325 A * | 1/2000 | Ma | ........................... | 73/24.02 |
| 6,036,362 A * | 3/2000 | Schmitt | ....................... | 378/206 |
| 6,233,307 B1 * | 5/2001 | Golenhofen | .................. | 378/45 |
| 6,292,532 B1 * | 9/2001 | Kawahara et al. | ............. | 378/49 |
| 6,614,878 B2 * | 9/2003 | Bogatu et al. | ................ | 378/158 |
| 6,633,627 B2 * | 10/2003 | Horiuchi | ..................... | 378/156 |
| 6,668,039 B2 * | 12/2003 | Shepard et al. | ................ | 378/47 |
| 7,065,174 B2 * | 6/2006 | Sipila et al. | .................... | 378/44 |
| 2007/0274441 A1 * | 11/2007 | Fukai et al. | .................... | 378/45 |

(Continued)

FOREIGN PATENT DOCUMENTS

JP     53-46065 Y2     11/1978

(Continued)

OTHER PUBLICATIONS

International Preliminary Report issued May 8, 2007.

*Primary Examiner*—Allen C. Ho
(74) *Attorney, Agent, or Firm*—Brinks Hofer Gilson & Lione

(57) ABSTRACT

A sample sealing vessel 8 includes a plurality of wall faces comprising a material for transmitting X-ray, an X-ray source 1 is arranged at a wall face 11 to irradiate primary X-ray, a face 12 different from the face irradiated with the primary X-ray is arranged to be opposed to an X-ray detector 10, and the primary X-ray from the X-ray source 1 is arranged to be able to irradiate the wall face 12 of the sample sealing vessel to which the X-ray detector 10 is opposed.

16 Claims, 7 Drawing Sheets

U.S. PATENT DOCUMENTS

2008/0013681 A1 *   1/2008   Fukai et al. .................. 378/44

FOREIGN PATENT DOCUMENTS

| | | |
|---|---|---|
| JP | 62-75241 A | 4/1987 |
| JP | 5-92703 U | 12/1993 |
| JP | 6-249804 A | 9/1994 |
| JP | 10-38772 A | 2/1998 |
| JP | 11-201917 A | 7/1999 |
| JP | 2000-55839 A | 2/2000 |
| JP | 2001-83110 A | 3/2001 |
| JP | 2004-150990 A | 5/2004 |

* cited by examiner

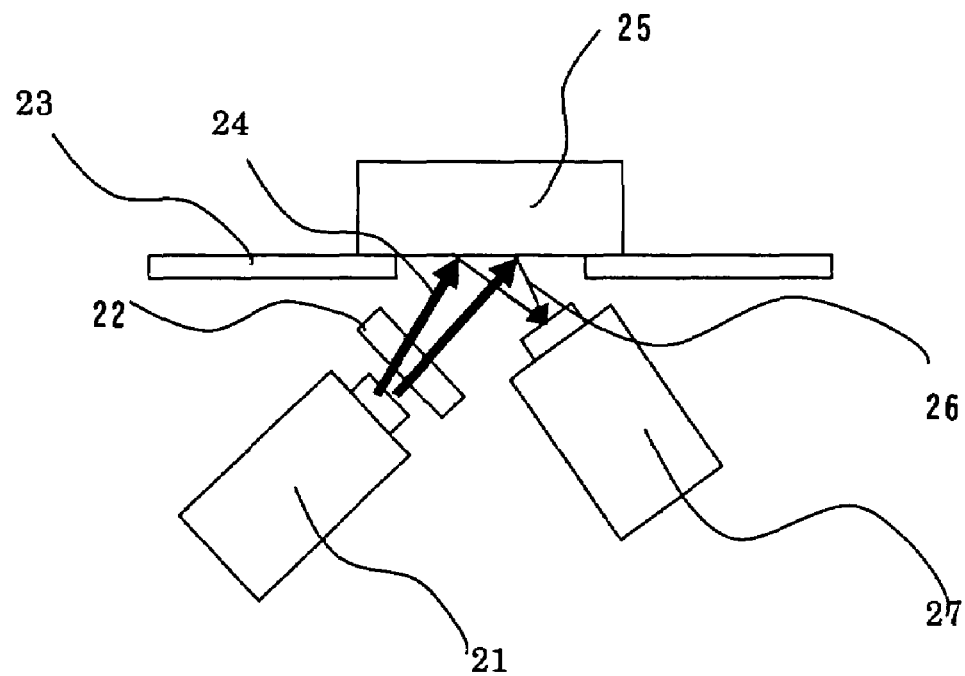
Fig-2
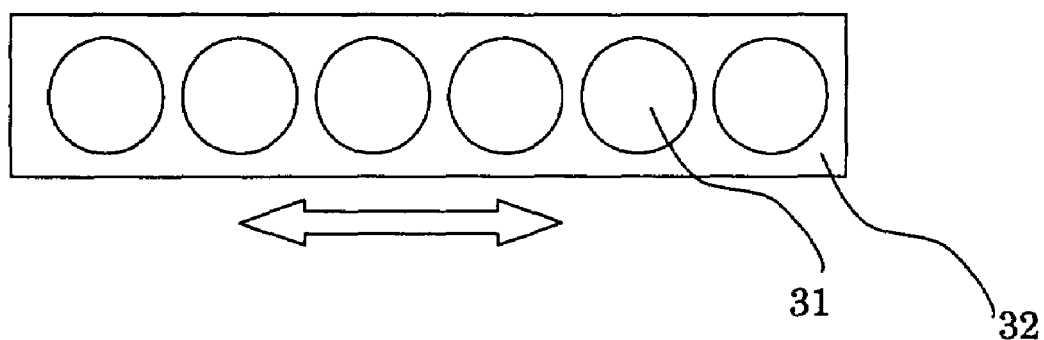
Fi-3

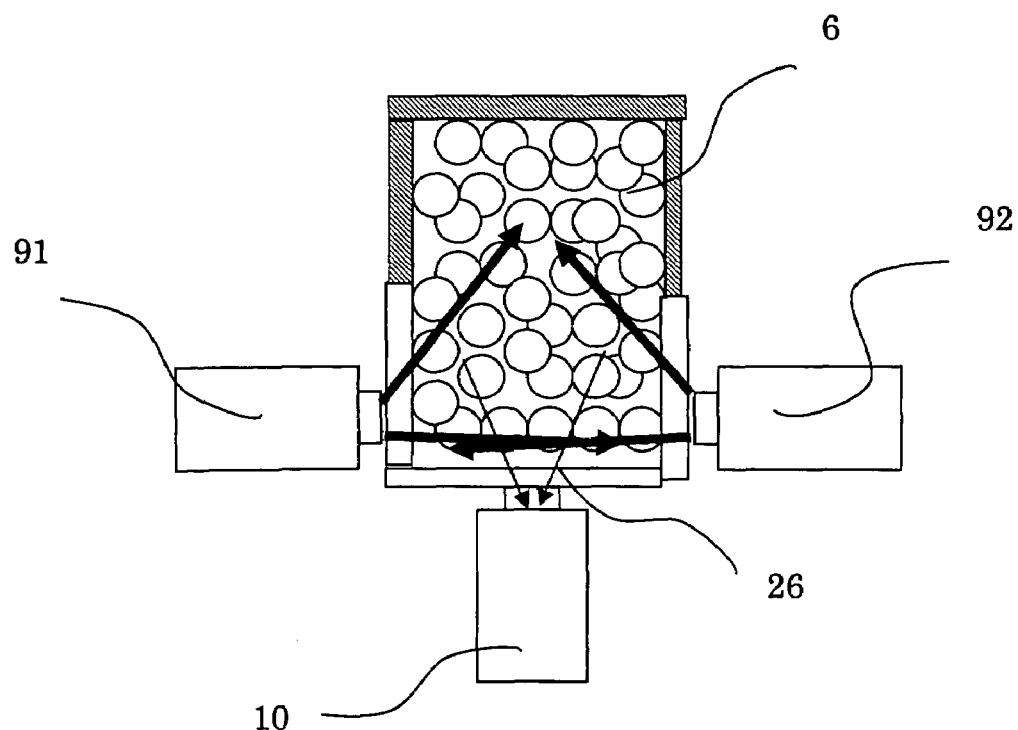
Fi-9
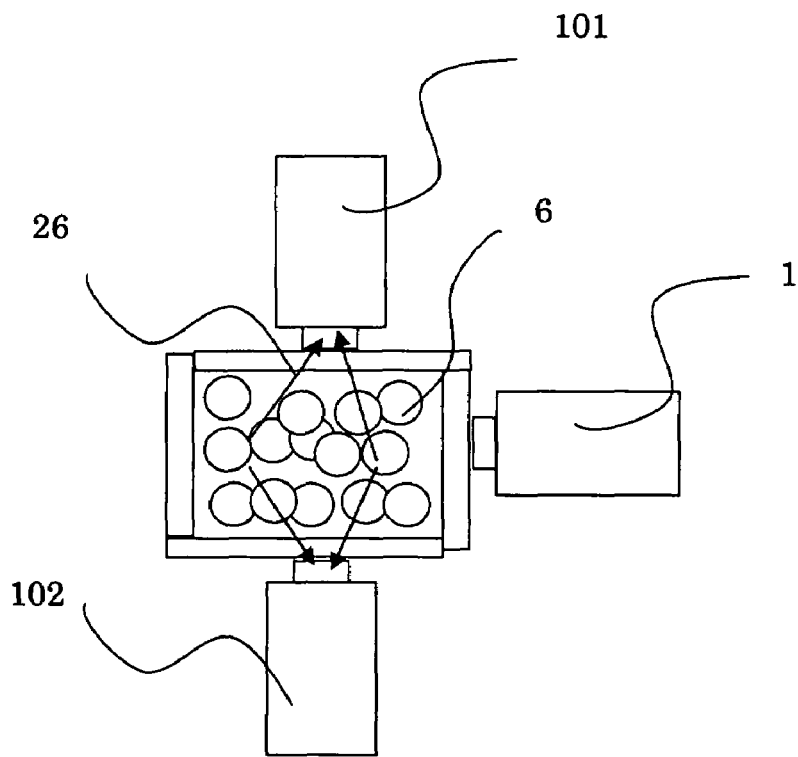
Fig-10

FLUORESCENT X-RAY ANALYSIS APPARATUS

This application is a continuation of PCT/JP2005/019658, filed Oct. 26, 2005, which claims priority to Japanese Application No. JP2004-323186, filed Nov. 8, 2004. The entire contents of these applications are incorporated herein by reference.

FIELD OF THE INVENTION

The present invention relates to a fluorescent X-ray analysis apparatus by irradiating a measurement sample with primary X-ray to induce to generate fluorescent X-ray from the measurement sample and measuring an energy and an X-ray intensity of the fluorescent X-ray to thereby carry out element analysis/composition analysis of the sample.

BACKGROUND OF THE INVENTION

A general fluorescent X-ray analysis apparatus of a background art will be explained in reference to FIG. 2. A measurement sample 25 is arranged on an upper side of a measurement sample base 23, and an X-ray source 21, a primary filter 22, an X-ray detector 27 are arranged on a lower side of the measurement sample base 23 by interposing the horizontal measurement sample base 23 therebetween, and a position to which the primary X-ray 24 is irradiated and a position to which the X-ray detector 27 for detecting fluorescent X-ray 26 constitute the same point. Further, it is general to increase a sensitivity of fluorescent X-ray from a heavy metal to which attention is paid by making the X-ray detector and the X-ray source 21 as proximate to the measurement sample as possible. Further, although in order to increase a ratio of a peak intensity of the fluorescent X-ray 26 for the element to which the attention is paid to a background intensity mainly by a scattered ray (hereinafter, peak background ratio), there are present an apparatus for pulling the primary filter 22, an apparatus using a secondary target, an apparatus using an optical element for constituting monochromatic light by X-ray, an optical element for converging X-ray, all of the apparatus are constituted by a structure of directing the X-ray detector to the point to which the primary X-ray is irradiated (refer to, for example, JP-A-2004-1 50990(page 3, FIG. 1)).

SUMMARY OF THE INVENTION

According to the fluorescent X-ray analysis apparatus of the background art, it is general to increase the peak background ratio by using the primary filter when presence or a concentration of a small amount of a heavy metal of cadmium or the like included in a main component of a light element constituted by C, O, H or the like. Although the method is very effective, the primary X-ray is attenuated by inserting the primary filter, as a result, an intensity of the fluorescent X-ray of the small amount of the heavy metal excited by the measurement sample incident on the X-ray detector is made to be small. Although in order to increase the intensity of the X-ray incident on the X-ray detector, the X-ray source and the X-ray detector are arranged to be proximate to the measurement sample, since both members are arranged to be directed to the same point, when both members are made to be proximate thereto, by an interference between structures of both members, there is a limit in a distance of making both members proximate thereto. Therefore, when the small amount of the heavy metal in the light element is measured, it is general that a lower limit of detection is several wt ppm by measurement of several 100 seconds.

Although in order to increase the limit of detection of the small amount of the heavy metal, also the peak background ratio constitutes an important factor, a magnitude of an X-ray intensity which can be acquired, in other words, also the sensitivity constitutes an important factor. A general equation of the limit of detection will be described as follows. When the X-ray intensity is increased, also the BG intensity (background intensity) and the sensitivity are increased in proportion thereto. That is, the lower limit of detection is inversely proportional to the X-ray intensity which can be acquired to improve the lower limit of detection.

$$\text{lower limit of detection} = 3 * (\text{BG intensity}/\text{measurement time})^{1/2}/\text{sensitivity}$$

According to the invention, in a fluorescent X-ray analysis apparatus, it is a problem to improve a lower limit of detection by effectively improving a peak background ratio without reducing an X-ray intensity which can be acquired by a detector.

In order to resolve the above-described problem, according to a fluorescent X-ray analysis apparatus of the invention, there is provided a fluorescent X-ray analysis apparatus which is a fluorescent X-ray analysis apparatus comprising a sample sealing vessel for sealing a solid or a liquid sample having a flowability, an X-ray source for irradiating the sample with a primary X-ray, and a detector for detecting a fluorescent X-ray generated from the sample irradiated with the primary X-ray, wherein an element analysis of the sample is carried out from a spectrum of the detected fluorescent X-ray, wherein the sample sealing vessel includes a plurality of wall faces comprising a material of transmitting the X-ray, arranged such that the primary X-ray is irradiated to a face thereof having the wall face, arranged such that a face different from the face irradiated with the primary X-ray is opposed to the X-ray detector, and arranged such that the primary X-ray from the X-ray source can irradiate the wall face of the sample sealing vessel to which the X-ray detector is opposed.

Thereby, the X-ray source and the X-ray detector can be made to be proximate to the surface of the sample sealing vessel to be brought into close contact therewith, the primary X-ray from the X-ray source can be irradiated to the sample sealing vessel widely by a high density, further, the fluorescent X-ray radially generated from the element to which the attention is paid of the measurement sample can efficiently be made to be incident on the detector. That is, an intensity of the X-ray of the element to which the attention is paid, which can be acquired by the X-ray detector can be increased, and a heavy metal included in a light element can be detected by a preferable sensitivity.

As the reason that the X-ray source and the X-ray detector of the fluorescent X-ray analysis apparatus of the background art are directed to the same point of the surface of the measurement sample, it is pointed out that a measurement sample whose major component is a heavy element of a Cu alloy, Fe alloy or the like is included as an object of the measurement. When the major component is the heavy metal, only the fluorescent X-ray generated by exciting the primary X-ray generated at an extreme surface can be escaped to outside of the sample. The reason is that the fluorescent X-ray is absorbed by the major component of the heavy metal. Therefore, even when the primary X-ray is irradiated from the outer wall of the side face of the sample sealing vessel and the X-ray detector is arranged at the outer wall of the bottom face of the sample sealing vessel as in the invention, the fluorescent X-ray from the measurement sample is not incident on the X-ray detector at all. According to the invention, an object is constituted by analysis of the heavy metal in an organic material or a light metal of aluminum, silicon, magnesium or the lie, and therefore, the primary X-ray from the X-ray source arranged at the side face relative to the measurement sample permeates inside of the sample, the fluorescent X-ray can be generated by exciting the heavy metal included at inside of the sample, the fluorescent X-ray generated at inside of the sample can be transmitted through the sample and can be incident on the X-ray detector arranged at the bottom face relative to the measurement sample.

On the other hand, there is mounted a primary filter for selectively exciting the heavy metal to which the attention is paid and reducing the background between the X-ray tube and the measurement sample. Thereby, also the peak background ratio when the spectrum is acquired by the X-ray detector can be improved.

Further, on an outer side of the measurement sample, a region other than a region of transmitting the primary X-ray and a region of transmitting the fluorescent X-ray generated from the measurement sample in being incident on the detector, is surrounded by a metal for generating the fluorescent X-ray optimum for exciting the heavy metal to which the attention is paid. Thereby, an efficiency of exciting the element to which the attention is paid is increased, the peak background ratio when the spectrum is acquired by the X-ray detector can be improved and the intensity of the fluorescent X-ray of the element to which the attention is paid can be increased.

Furthermore, there is mounted a secondary filter for selectively transmitting only the fluorescent X-ray from the element to which the attention is paid between the measurement sample and the X-ray detector. Thereby, the peak background ratio when the spectrum is acquired by the X-ray detector can be improved and a saturated state of the X-ray detector by making a large amount of X-ray incident thereon can be prevented.

Further, by replacing the sample sealing vessel by a measurement sample chamber having a similar shape, a similar structure can be adopted by directly filling the sample to the measurement sample chamber.

BRIEF DESCRIPTION OF THE DRAWINGS

FIG. 2 is a schematic view of a general fluorescent X-ray analysis apparatus of a background art.

FIG. 3 is a schematic view of primary/secondary filter blocks having a plurality of filters.

FIG. 9 is a schematic view of a fluorescent X-ray analysis apparatus having a plurality of X-ray sources.

FIG. 10 is a schematic view of a fluorescent X-ray analysis apparatus having a plurality of X-ray detectors.

DETAILED DESCRIPTION OF THE PREFERRED EMBODIMENTS

Embodiments of the invention will be explained in reference to the drawings.

Figure 8:
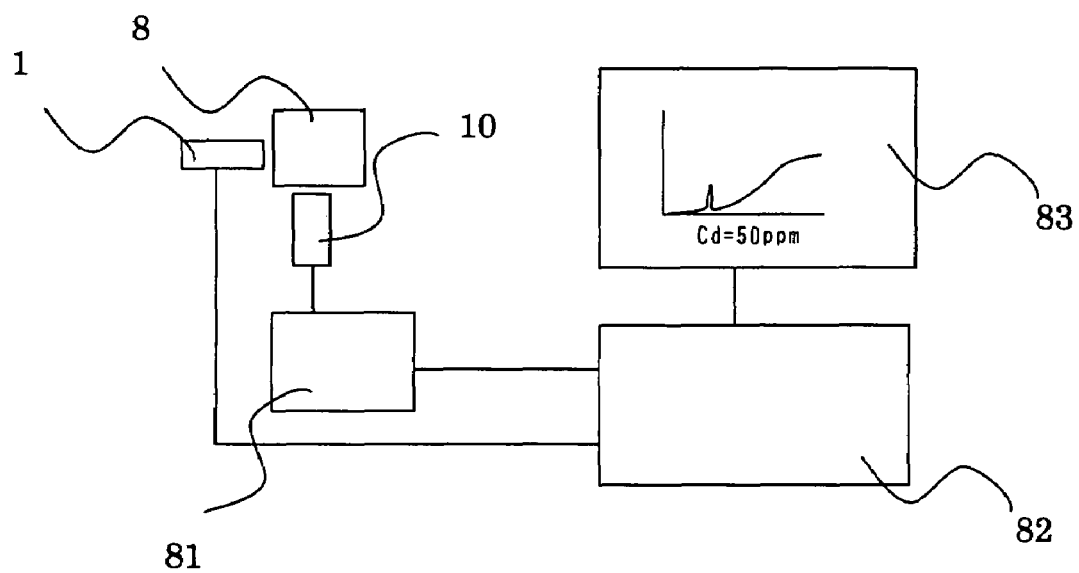
FIG. 8 is a block diagram of a fluorescent X-ray analysis apparatus.

FIG. 8 is a block diagram of a fluorescent X-ray analysis apparatus according to the invention. The X-ray source 1 is controlled by the control portion/computer portion 82 to irradiate primary X-ray onto a sample sealing vessel 8 and secondary X-ray from the sample sealing vessel 8 is acquired by the X-ray detector 10. X-ray incident on the X-ray detector 10 is converted into an electric signal by the amplifier/waveform shaper portion 81, converted into intensity spectra for respective energies by the control portion/computer portion 82 and is displayed on the monitor 83. Further, a concentration is also calculated by spectra information at the control portion/computer portion 82 and also the information is displayed on the monitor 83.

Figure 1:
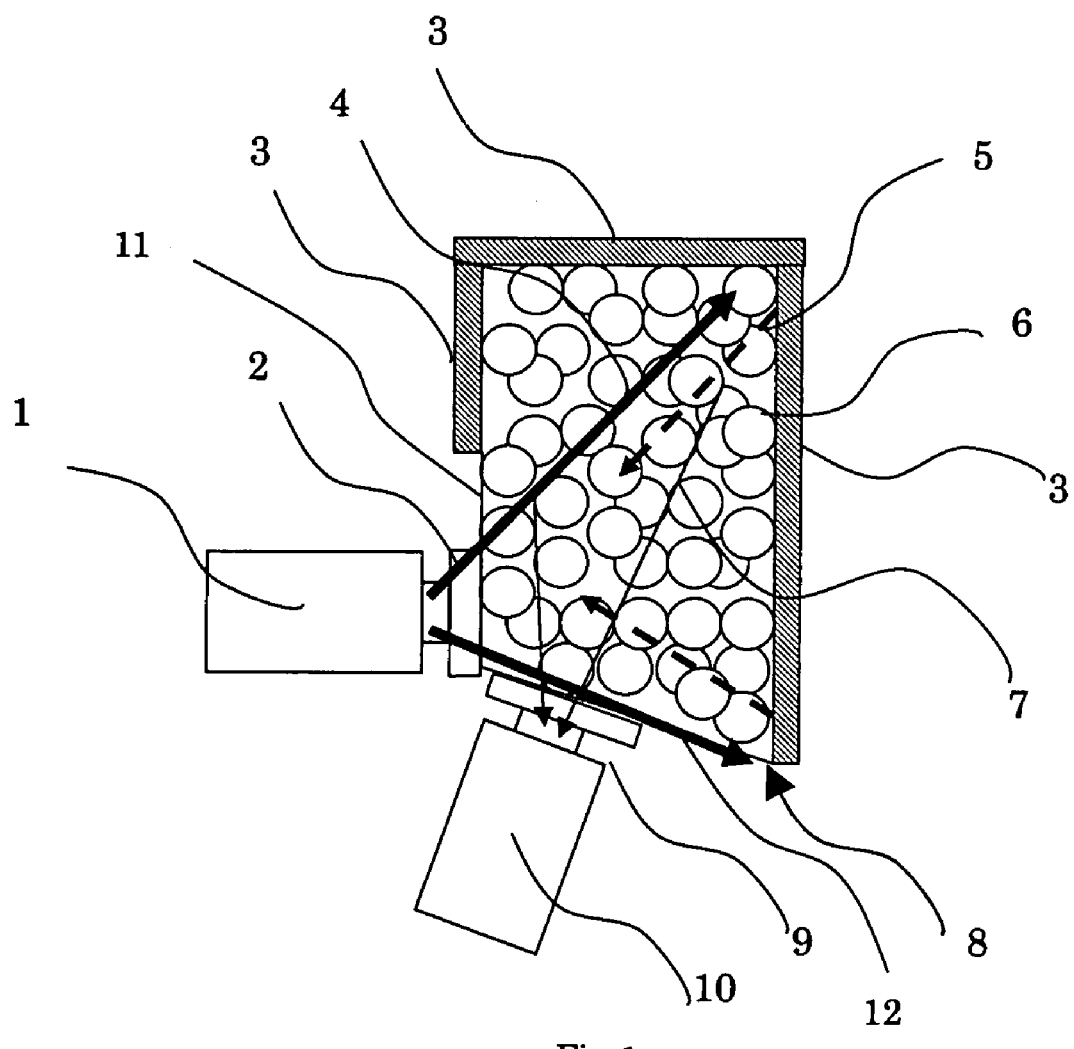
FIG. 1 is a schematic view of a portion of a fluorescent X-ray analysis apparatus.

FIG. 1 is a schematic view of an X-ray optical system of a fluorescent X-ray analysis apparatus according to the invention. In FIG. 1, a small amount of the grain-like measurement sample 6 including a heavy metal is filled in the sample sealing vessel 8 comprising an organic material or a material of aluminum, silicon, magnesium or the like through which X-ray is transmitted comparatively easily. The grain-like measurement sample is set to the analysis apparatus along with the sample sealing vessel 8. According to the invention, a center of a point of a surface of the measurement sample to which the primary X-ray 4 from the X-ray source 1 is irradiated, and a point of the surface of the sample to which the X-ray detector 10 is directed differ from each other, and therefore, the X-ray source 1 and the X-ray detector 10 can be brought into close contact with the sample sealing vessel 8. The X-ray source 1 is brought into close contact with a side face 11 of the sample sealing vessel 8, the X-ray detector 10 is brought into close contact with a bottom face 12 of the sample sealing vessel 8. Further, both members are arranged such that the primary X-ray 4 from the X-ray source 1 is irradiated to a vicinity of the bottom face 12 of the sample sealing vessel 8 with which the X-ray detector 10 is brought into close contact. The primary X-ray 4 generated from the X-ray source 1 transmits through the primary filter 2 suitable for excitation and improvement of a peak background ratio of an element to which attention is paid, is incident on an outer wall of the side face 11 of the sample sealing vessel 8 and is irradiated to the measurement sample 6. The primary X-ray 4 generated from the point which is very proximate to the measurement sample 6 constitutes a large solid angle from the X-ray source 1 to the measurement sample 6, and therefore, the primary X-ray 4 can efficiently excite the small amount of the heavy metal at inside of the measurement sample 6. A portion of the fluorescent X-ray 7 from the element to which the attention is paid, which is radially generated from the small amount of the heavy metal transmits through the measurement sample 6 whose major component is light element and is incident on the X-ray detector 10. The X-ray detector 10 is brought into close contact with the sample sealing vessel 8, and therefore, a solid angle constituted from the measurement sample 6 to the X-ray detector 10 is large, and therefore, the fluorescent X-ray 7 from the element to which the attention is paid can efficiently be incident on the X-ray detector 10, and a sensitivity can be increased.

On the other hand, in a vessel wall of the sample sealing vessel 8, other than a region of transmitting the primary X-ray 4, and a region of transmitting the fluorescent X-ray 7 directed to the X-ray detector 10 is constituted by the secondary exciting wall 3 constituted by an element for generating fluorescent X-ray optimum for exciting the small amount of the heavy metal. A large portion of the primary X-ray 4 transmits through the comparatively light measurement sample 6 without an interactive operation therebetween. The transmitted primary X-ray 4 excites the secondary exciting wall 3 to generate the secondary exciting fluorescent X-ray 5 optimum for exciting the small amount of the heavy metal. The secondary exciting fluorescent X-ray 5 efficiently excites a small amount of a harmful metal at inside of the measurement sample 6 to improve the peak background ratio of the spectrum of the small amount of the heavy metal when acquired by the X-ray detector 10.

Further, by mounting the secondary filter 9 for selectively transmitting the fluorescent X-ray 7 from the element to which the attention is paid between the sample sealing vessel 8 and the X-ray detector 10, the peak background ratio of the spectrum of the small amount of the heavy metal can be improved and a saturated state by an enormous amount of X-ray detection by the X-ray detector 10 can be prevented.

FIG. 3 is a schematic view of a primary filter block or a secondary filter block having a plurality of filters. According to the primary filter 2 of FIG. 1, by switching a filter used by a filter block having a plurality of kinds of the filters 31 as shown by FIG. 3 and a system of driving the same, even when there are a plurality of elements at which the attention is paid, exciting efficiencies optimum for the elements to which the attention is paid can be realized.

Also with regard to the secondary filter 9 of FIG. 1, similarly, as shown by FIG. 3, by switching a filter used by a filter block in which the plurality of kinds of filters 31 are mounted to the filter base 32 and a system for driving the same, even when there are a plurality of elements to which the attention is paid, fluorescent X-ray from the elements to which the attention is paid can selectively be transmitted.

Also with regard to the secondary exciting wall 3 of FIG. 1, by similarly including a plurality of secondary exciting walls and a switching mechanism, even when there are a plurality of elements at which the attention is paid, exciting efficiencies optimum for the elements at which the attention is paid can be realized.

Even when there is not the sample sealing vessel 8 of FIG. 1, the effect of the invention can be realized by constituting a shape of a measurement sample chamber by a shape similar to that of the sample sealing vessel 8 and filling the measurement sample chamber with a measurement sample.

A shape of the sample sealing vessel 8 of FIG. 1 and a shape of the measurement sample chamber when the sample sealing vessel 8 is not used are only examples, and when there can be realized an arrangement in which the primary X-ray 4 is irradiated to a vicinity of a face with which one or both of the X-ray detector 10 and the X-ray source 1 is (are) brought into close contact and with which the X-ray detector 10 is brought into contact, even by an arbitrary shape, the effect of the invention can be realized.

Even when any one or a plurality of the primary filter 2, the secondary exciting wall 3, the secondary filter 9 of FIG. 1 is (are) not provided, a portion of the effect of the invention can be realized.

Figure 4:
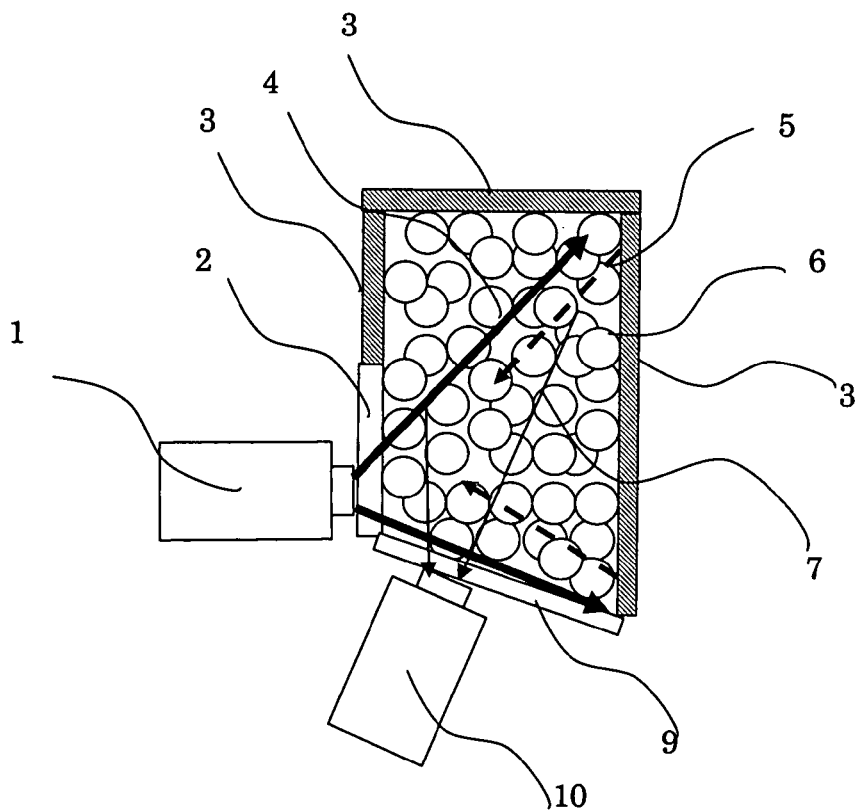
FIG. 4 is a schematic view of a portion of a fluorescent X-ray analysis apparatus when a sample sealing vessel is constituted by primary filter/secondary exciting wall/secondary filter.

FIG. 4 is a schematic view of a portion of a fluorescent X-ray analysis apparatus when a sample sealing vessel is constituted by the primary filter 2/the secondary exciting wall 3/the secondary filter 9. As shown by FIG. 4, by establishing a portion of an outer wall of the sample sealing vessel 8 by any one or a plurality of the primary filter 2, the secondary exciting wall 3, the secondary filter 9, the X-ray source 1 and the X-ray detector 10 can be made to be proximate to the sample sealing vessel 8 the most, and the effect of the invention can maximally be achieved.

A characteristic of the invention resides in that the point of the surface of the measurement sample 6 to which the X-ray source 1 is directed and the point to which the X-ray detector 10 is directed are disposed at different locations. Therefore, although according to the embodiment, the X-ray source 1 is arranged at the outer wall of the side face of the sample sealing vessel 8 and the X-ray detector 10 is arranged at the outer wall of the bottom face of the sample sealing vessel 8, so far as the characteristic that the point of the wall face of the sample sealing vessel 8 to which the X-ray source is directed and the point to which the X-ray detector is directed differ from each other is satisfied, the X-ray source can be arranged at a face different from the outer wall of the side face, or the X-ray detector can also be arranged at a face different from the outer wall of the bottom face.

FIG. 9 is a schematic view of a portion of a fluorescent X-ray analysis apparatus having a plurality of X-ray sources. As shown by FIG. 9, by including a plurality of the X-ray sources 91, 92, an efficiency of exciting an element to which the attention is paid of the measurement sample 6 can be increased, by increasing an intensity of fluorescent X-ray 26 from the element to which the attention is paid, an intensity of X-ray incident on the X-ray detector 10 can be increased and a lower limit of detection can be improved.

FIG. 10 is a schematic view of a portion of a fluorescent X-ray analysis apparatus having a plurality of X-ray detectors. As shown by FIG. 10, by including a plurality of the X-ray detectors 101, 102, the fluorescent X-ray 26 from the element to which the attention is paid of the measurement sample 6 can efficiently be acquired, a total of an X-ray intensity can be increased, and the lower limit of detection can be improved.

Figure 11:
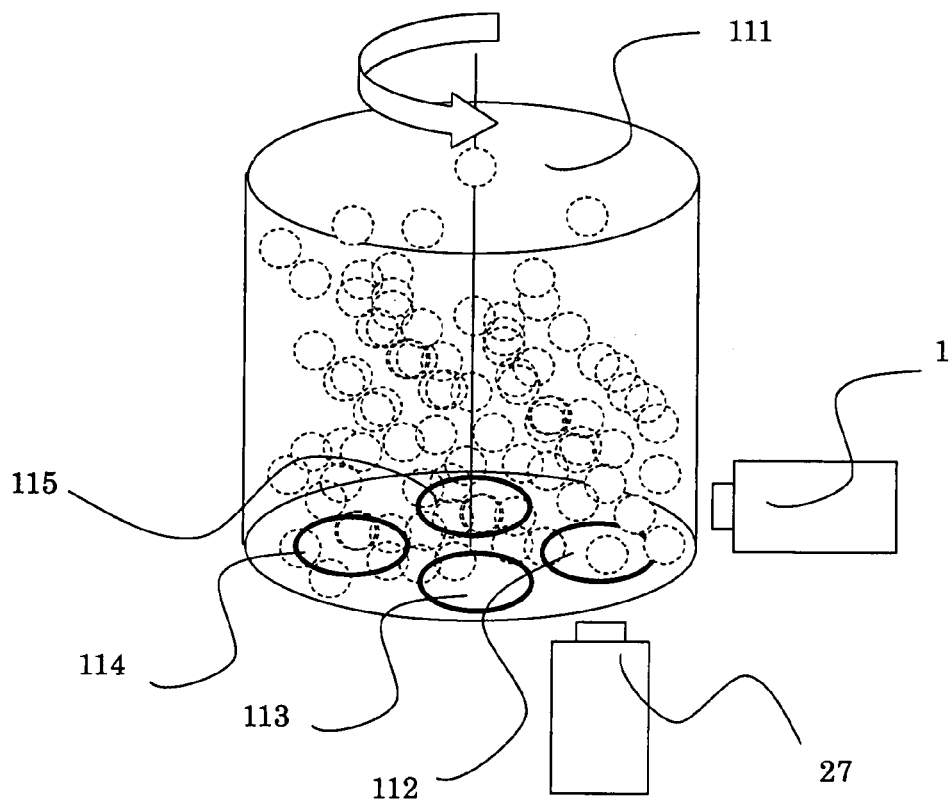
FIG. 11 is a schematic view of a fluorescent X-ray analysis apparatus having a plurality of secondary filters in a sample vessel and switching the secondary filters by driving to rotate the sample vessel.

FIG. 11 is a schematic view of a portion of a fluorescent X-ray analysis apparatus including a plurality of secondary filters in a sample vessel and switching the secondary filters by driving a sample vessel. When there are a plurality of the elements to which the attention is paid, as shown by FIG. 11, by mounting a plurality of the secondary filters 112, 113, 114, 115 at the sample vessel 111 per se and driving to rotate the secondary filters around a center axis of the vessel per se, the secondary filters can be changed. Normally, it is preferable that the sample vessel 111 and the detector 27 are proximate to each other. When a plurality of secondary filters and a secondary filter driving portion are provided at other than the sampler vessel, by a space thereof, a distance between the sampler vessel and the detector is increased to deteriorate the lower limit of detection. However, by providing the plurality of secondary filters at the sample vessel 111 per se as shown by FIG. 11, the change of the plurality of secondary filters can be realized without increasing the distance from the X-ray detector 27.

Figure 12:
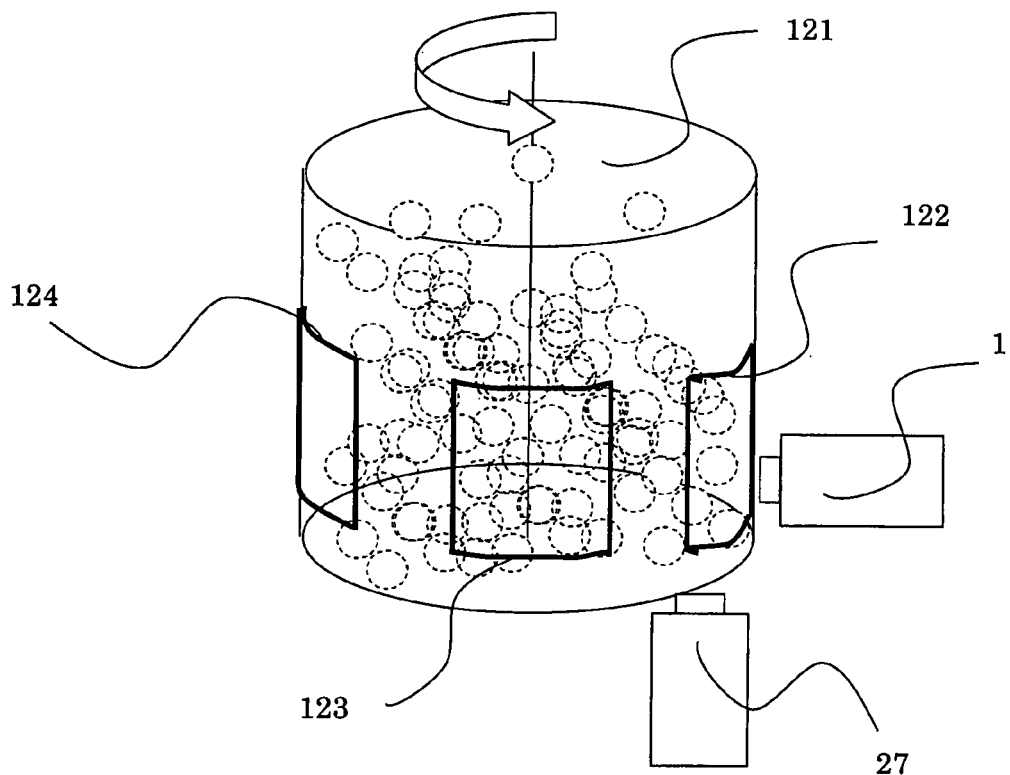
FIG. 12 is a schematic view of a fluorescent X-ray analysis apparatus having a plurality of primary filters in a sample vessel and switching the primary filters by driving to rotate the sample vessel.

FIG. 12 is a schematic view of a portion of a fluorescent X-ray analysis apparatus including a plurality of primary filters and switching the primary filters by driving the sample vessel. When there are a plurality of elements to which the attention is paid, as shown by FIG. 11, a plurality of the primary filters 122, 123, 124 are mounted to the sample vessel 121 per se, and the primary filters can be changed by driving to rotate the primary filters around a center axis of the vessel per se. Normally, it is preferable that the sample vessel 121 and the X-ray source 1 are proximate to each other. When the plurality of primary filters and a primary filter driving portion are provided at a location other than the sample vessel, by a space thereof, a distance between the sample vessel and the X-ray source is increased to deteriorate the lower limit of detection. However, by providing the plurality of primary filters at the sample vessel 121 per se as shown by FIG. 12, the change of the plurality of primary filters can be realized without increasing the distance from the X-ray source 1.

Figure 13:
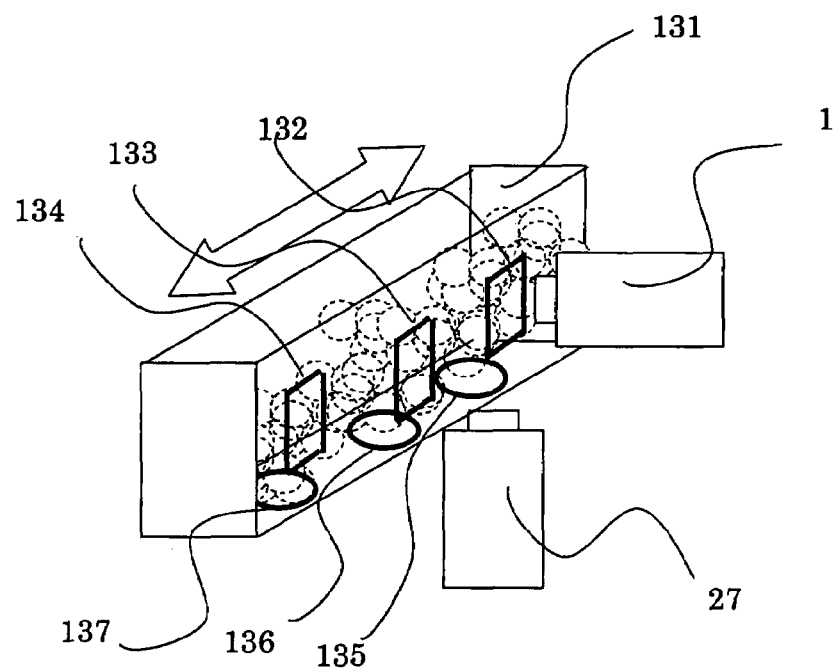
FIG. 13 is a schematic view of a fluorescent X-ray analysis apparatus having a plurality of primary filters or secondary filters in a sample vessel and switching the filters by linearly driving the sample vessel.

By mounting a plurality of the primary filters 132, 133, 134 or a plurality of the secondary filters 135, 136, 137 at the sample vessel 131 as shown by FIG. 13, with an object of the same as those of contents described in reference to FIG. 11 and FIG. 12, and linearly driving the vessel per se, the primary filters or the secondary filters can be realized to enable to change.

Figure 14:
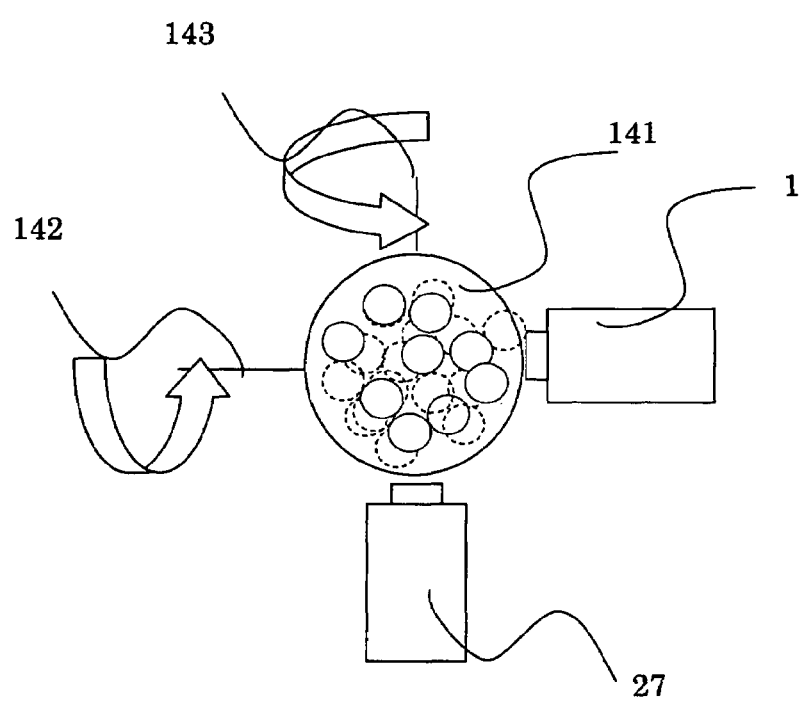
FIG. 14 is a schematic view of a fluorescent X-ray analysis apparatus having a biaxial rotating mechanism in a sample vessel.

FIG. 14 is a schematic view of a portion of a fluorescent X-ray analysis apparatus having a biaxial rotating mechanism at a sample vessel. As shown by FIG. 14, by filling the spherical sample vessel 141 with a sample and measuring by rotating by the monoaxial or biaxial rotating mechanisms 142, 143, even when a distribution of a concentration of a measurement sample is nonuniform, averaged concentration information can be acquired. Further, even when the sample per se is spherical, the same object can be achieved by rotating the sample per se.

Figure 5:
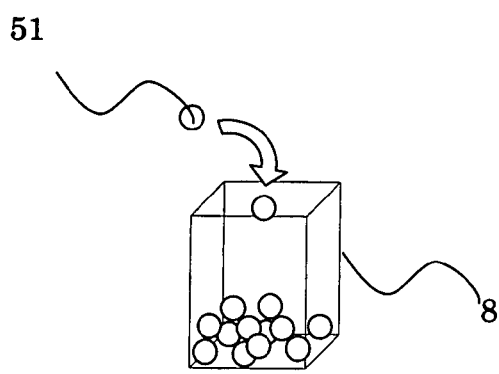
FIG. 5 is a schematic view of filling a sample sealing vessel with a grain constituting a measurement sample.
Figure 6:
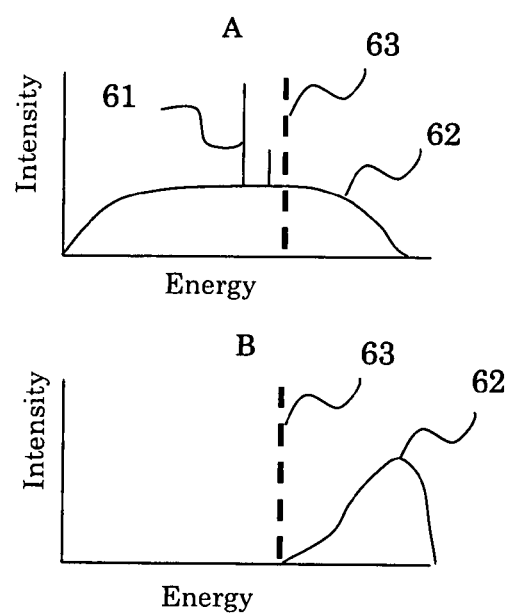
FIG. 6 illustrates schematic diagrams of a changing a quality of X-ray from an X-ray source by a primary filter.

An embodiment of the invention will be described as follows by taking an example of analysis of Cd in a grain. FIG. 5 is a schematic view of filling a sample sealing vessel with a grain constituting the measurement sample. As shown by FIG. 5, the sample sealing vessel 8 is filled with the grain 51 including Cd. As shown by FIG. 1, the sample sealing vessel 8 filled with the grain 51 including Cd is set to a space surrounded by the primary filter 2, the secondary exciting wall 3, the secondary filter 9. When an X-ray tube is used as the X-ray source 1, a relationship between an energy and an intensity of X-ray generated from the X-ray tube (hereinafter, spectrum) generally becomes as shown by A of FIG. 6 That is, the spectrum is constituted by the characteristic X-ray 61 and the continuous X-ray 62 of a target of the X-ray tube. Kα fluorescent X-ray of Cd is present at a position of about 23 keV indicated by numeral 63. The characteristic X-ray 61 and the continuous X-ray 62 are scattered at the grain 51 substantially in a radial shape. The X-ray scattered in the radial shape is incident also on the X-ray detector 10 to increase a background of Cd. When the background is increased, the detection limit is deteriorated, and fluorescent X-ray of a small amount of Cd cannot be detected. Therefore, the primary filter 2 comprising Mo, Zr or the like is arranged between the X-ray tube and the sample sealing vessel 8. A low energy side is absorbed by the primary filter 2, and a spectrum of X-ray from the X-ray tube becomes as shown by B of FIG. 6, and the characteristic X-ray 61 and the continuous X-ray at a periphery of the Cd energy position 63 are reduced. Thereby, also the intensity by which the X-ray is incident on the X-ray detector 10 is reduced, and therefore, the background of Cd is reduced and the detection limit is increased.

The continuous X-ray 62 transmitting through the primary filter and having a large rate of a high energy excites Cd at inside of the grain 51 to generate the fluorescent X-ray 7 of Cd. The X-ray detector 10 can be made to be proximate to the sample sealing vessel 8 without taking an interference with the X-ray tube 1 into consideration, and therefore, the fluorescent X-ray 7 generated from Cd in the grain and generated radially can efficiently be detected by the X-ray detector 10.

Further, in FIG. 1, a large portion of the continuous X-ray 62 transmitting through the primary filter and having the large rate of the high energy passes through the grain comprising the light element and is irradiated to the secondary exciting wall 3. When a material of the secondary exciting wall 3 is constituted by Te or the like which is efficient for exciting K radiation fluorescent X-ray of Cd and generates a slightly large energy from an absorption end of 26.7 keV by energy, fluorescent X-ray of 27.4 keV is generated from the secondary exciting wall 3 radially from the wall face to the grain. The fluorescent X-ray of 27.4 keV can selectively excite Cd in the grain, as a result, the intensity of the fluorescent X-ray of Cd incident on the X-ray detector can be increased. Although there is frequently observed a case of arranging such a secondary exciting wall between the X-ray source and the measurement sample even in fluorescent X-ray of the background art, the present invention is characterized in that the measurement sample is arranged between the X-ray source and the secondary exciting wall.

Figure 7:
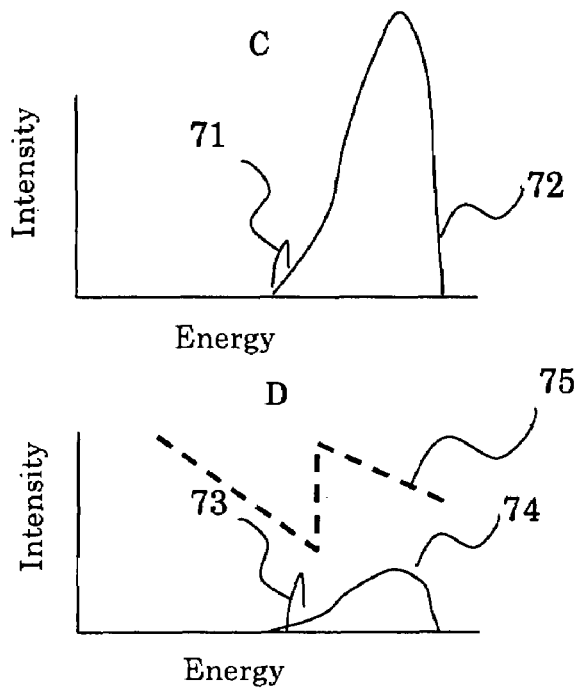
FIG. 7 illustrates schematic diagrams of changing a quality of X-ray from a measurement sample by a secondary filter.

Fluorescent X-ray of Cd generated from the grain and detected by the detector and the scattering X-ray of the continuous X-ray become as shown by C of FIG. 7 in spectra. The spectra are constituted by the peak 71 of the fluorescent X-ray of Cd and the broad mountain 72 of scattering ray of the continuous X-ray. On the other hand, normally, in the X-ray detector, a number of capable of counting per unit time is determined, when a number equal to or larger than the number of X-ray is incident, a number capable of being counted actually is reduced, and the efficiency is deteriorated. Hence, by arranging Ag (absorbing curve of Ag is indicated by numeral 75) having an absorption end at an energy slightly larger than that of the energy of Kα of Cd of about 23 keV between the sample sealing vessel 8 and the X-ray detector 10 as the secondary filter 9, a large portion of Kα of Cd is not absorbed by the secondary filter 9, a large portion of scattering X-ray of a higher energy is absorbed, thereby, as shown by D of FIG. 7, an intensity of X-ray having a particularly high energy of a total can be restrained as shown by the broad mountain 74 such that the peak 73 of Kα of Cd is not so reduced.

The invention achieves the effect as described below.

That is, the acquired intensity and the peak background ratio of the fluorescent X-ray to which the attention is paid are improved, and therefore, the lower limit of detection of the element to which the attention is paid can be improved. Further, the measurement time can be shortened by a level of the lower limit of detection which can be realized by the apparatus of the background art.

The invention claimed is:

1. A fluorescent X-ray analysis apparatus comprising:
   at least one X-ray source configured to emit an X-ray:
   at least one X-ray detector configured to detect a fluorescent X-ray; and
   a sample container configured to store a quantity of sample and comprising at least two non-coplanar, X-ray transmissive windows, wherein the at least one X-ray source is placed outside the sample container such that through one of the at least two windows, it irradiates the X-ray to interrogate the quantity of sample in the sample container, while the at least one X-ray detector is placed outside the sample container such that through another of the at least two windows, it detects the fluorescent X-ray emitted as a result of interrogation of the quantity of sample in the sample container.

2. A fluorescent X-ray analysis apparatus according to claim 1, wherein the at least one X-ray source is placed adjacent to the one of the at least two windows.

3. A fluorescent X-ray analysis apparatus according to claim 1, wherein the at least one X-ray detector is placed adjacent to said another of the at least two windows.

4. A fluorescent X-ray analysis apparatus according to claim 1, further comprising at least one filter configured to pass through an X-ray within a specific wavelength range.

5. A fluorescent X-ray analysis apparatus according to claim 4, wherein the at least one filter is provided to the at least one X-ray source.

6. A fluorescent X-ray analysis apparatus according to claim 4, wherein the at least one filter forms at least a part of the one of the at least two windows.

7. A fluorescent X-ray analysis apparatus according to claim 4, wherein the at least one filter is provided to the at least one X-ray detector.

8. A fluorescent X-ray analysis apparatus according to claim 4, wherein the at least one filter forms at least a part of said another of the last least two windows.

9. A fluorescent X-ray analysis apparatus according to claim 1, wherein except the at least two windows, the sample container is made at least partially with an X-ray fluorescent material.

10. A fluorescent X-ray analysis apparatus according to claim 1, wherein the sample container is made at least partially with a material which is responsive to the X-ray from the at least one X-ray source to emit a fluorescent X-ray for interrogation of the quantity of sample in the sample container.

11. A fluorescent X-ray analysis apparatus according to claim 1, wherein the X-ray source is placed such that the X-ray therefrom enters the sample container through the one of the at least two windows and at least partially irradiates said another of the at least two windows.

12. A fluorescent X-ray analysis apparatus according to claim 1, wherein the sample container is cylindrical in shape.

13. A fluorescent X-ray analysis apparatus according to claim 1, wherein the sample container is of a shape of elongated parallelogram.

14. A fluorescent X-ray analysis apparatus according to claim 1, wherein the sample container is movable along at least one direction.

15. A fluorescent X-ray analysis apparatus according to claim 1, wherein the sample container is rotatable about at least one axis.

16. A fluorescent X-ray analysis apparatus according to claim 1, wherein the one of the at least two windows is configured to come in contact with the sample in the sample container.

* * * * *

UNITED STATES PATENT AND TRADEMARK OFFICE
CERTIFICATE OF CORRECTION

| | |
|---|---|
| PATENT NO. | : 7,436,926 B2 |
| APPLICATION NO. | : 11/799992 |
| DATED | : October 14, 2008 |
| INVENTOR(S) | : Yoshiki Matoba et al. |

Page 1 of 1

It is certified that error appears in the above-identified patent and that said Letters Patent is hereby corrected as shown below:

On the Title Page

In column 1, Item (22), delete "May 3, 2007" and substitute --May 2, 2007-- in its place.

Signed and Sealed this

Second Day of December, 2008

JON W. DUDAS
*Director of the United States Patent and Trademark Office*